(12) United States Patent
Birkbeck

(10) Patent No.: US 8,343,158 B2
(45) Date of Patent: Jan. 1, 2013

(54) TOOL FOR FORMING A CAVITY WITHIN A BONE

(75) Inventor: Alec Paul Birkbeck, Leeds (GB)

(73) Assignee: Depuy International Limited (GB)

( * ) Notice: Subject to any disclaimer, the term of this patent is extended or adjusted under 35 U.S.C. 154(b) by 643 days.

(21) Appl. No.: 12/527,493

(22) PCT Filed: Feb. 14, 2008

(86) PCT No.: PCT/GB2008/000520
§ 371 (c)(1),
(2), (4) Date: Aug. 17, 2009

(87) PCT Pub. No.: WO2008/099187
PCT Pub. Date: Aug. 21, 2008

(65) Prior Publication Data
US 2010/0094296 A1  Apr. 15, 2010

(30) Foreign Application Priority Data
Feb. 15, 2007 (GB) .................................. 0702948.1

(51) Int. Cl.
*A61B 17/00* (2006.01)
(52) U.S. Cl. ....................................................... 606/80
(58) Field of Classification Search ............... 606/79–85
See application file for complete search history.

(56) References Cited

U.S. PATENT DOCUMENTS

| | | | |
|---|---|---|---|
| 3,915,169 A * | 10/1975 | McGuire | 606/83 |
| 4,475,852 A | 10/1984 | Koppelmann | |
| 4,722,338 A | 2/1988 | Wright | |
| 4,777,948 A * | 10/1988 | Wright | 606/83 |
| 5,443,475 A * | 8/1995 | Auerbach et al. | 606/170 |
| 6,425,896 B1 | 7/2002 | Baltschun | |
| 6,746,451 B2 * | 6/2004 | Middleton et al. | 606/79 |
| 6,923,813 B2 | 8/2005 | Phillips et al. | |
| 7,749,228 B2 * | 7/2010 | Lieberman | 606/84 |
| 8,034,088 B2 * | 10/2011 | Pagano | 606/279 |
| 2003/0220698 A1 | 11/2003 | Mears | |
| 2004/0208717 A1 | 10/2004 | Greenhalgh | |
| 2005/0240193 A1 | 10/2005 | Layne | |
| 2006/0074427 A1 * | 4/2006 | Lieberman | 606/84 |
| 2008/0114364 A1 * | 5/2008 | Goldin et al. | 606/79 |

FOREIGN PATENT DOCUMENTS

| | | |
|---|---|---|
| DE | 1215858 B | 5/1966 |
| WO | WO 0134040 A1 | 5/2001 |
| WO | WO 0160268 A1 | 8/2001 |
| WO | WO 2004052216 A1 | 6/2004 |

OTHER PUBLICATIONS

PCT International Search Report PCT/GB2008/000520 dated Aug. 28, 2008.
UK Search Report GB0702948.1 dated Jun. 29, 2007.

* cited by examiner

*Primary Examiner* — Nicholas Woodall

(57) ABSTRACT

A tool (2) for forming a cavity within a bone (6) comprises a shaft (10) and a blade (12) which is pivotally mounted on the shaft towards one end thereof. A rod is fastened to the blade, and can slide within the shaft, to change the pivotal position of the blade relative to the shaft. The tool can include an incremental drive to cause the rod to translate along the shaft when the shaft and rod are rotated.

8 Claims, 2 Drawing Sheets

TOOL FOR FORMING A CAVITY WITHIN A BONE

CROSS REFERENCE TO RELATED APPLICATION

Figure 1:
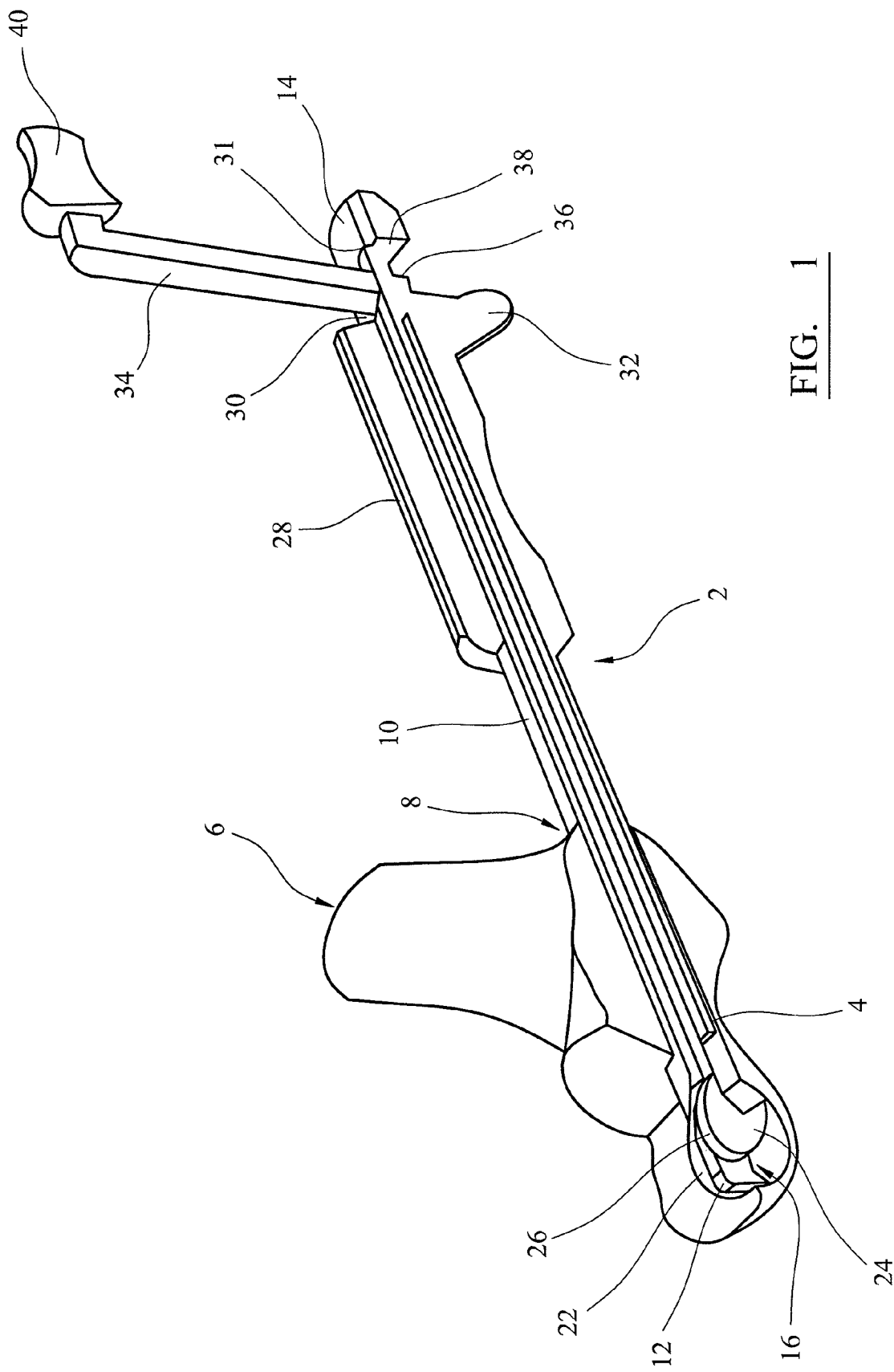

The present application is a continuation of International Patent Application PCT/GB2008/000520 filed Feb. 14, 2008.

This invention relates to a tool for forming a cavity within a bone.

It can be desirable to form a cavity within a bone during treatment of a bone defect. This can arise for example in a patient suffering from avascular necrosis (AVN), which is also known as osteonecrosis (ON), ischemic bone necrosis, or aseptic necrosis. AVN results from the temporary or permanent loss of circulation to the bone tissue, and gives rise to localized death of the bone tissue. The loss of proper blood flow can result from trauma, or compromising conditions such as prolonged steroid use, alcohol use, gout diabetes, pancreatitis, venous occlusion, decompression disease, radiation therapy, chemotherapy, and Gaucher's disease.

The condition can give rise to severe pain and limitation of movement within a short period, with a 70 to 80% chance of complete collapse of the bone and surrounding articulating surface after three years if left untreated. Joint replacement can be necessary for many patients.

Treatments for AVN which focus on salvaging the head of the femur or other bone or joint include core decompression, osteomy, bone grafting, and vascularized fibular grafting.

U.S. Pat. No. 6,679,890 discloses a method and device for treating AVN of the femoral head. The device disclosed in U.S. Pat. No. 6,679,890 augments the femoral head with bone cement. An open ended and fenestrated tube is inserted through a hole into the femoral neck and uncured bone cement is injected and cured at high pressure. The tube for injection of the cement is straight. In the disclosed technique, the cavity which is formed in the femur, extending through the neck into the head, has a constant cross-section, such as might be formed using a rotating drill or reamer or burr tool.

Frequently, the portion of a bone which is affected by AVN is concentrated in the superior anterior region of the femoral head. The affected portion can have a generally flat shape when the bone is viewed along the anterior-posterior axis. The width of the portion of a bone which is affected in this way can often be greater than the width of a tunnel which is required to gain axis to the portion of the bone to treat it.

In one aspect, the invention provides a tool for forming a cavity within a bone, which comprises:
a. a shaft,
b. a blade which is pivotally mounted on the shaft towards one end thereof,
c. a rod which is fastened to the blade, and which can slide within the shaft, to change the pivotal position of the blade relative to the shaft.

The tool of the invention has the advantage that a blade can be moved at the end of a shaft between a retracted orientation and a deployed orientation. Accordingly, the tool permits location of the blade through a small diameter tunnel, before being deployed in a desired location to form a cavity in that location. The resulting cavity can be wider than the tunnel through which access is gained to the affected bone tissue.

Preferably, the tool includes a lever for changing the position of the rod within the shaft. For example, it can be preferred for the lever to have first and second ends, and to be mounted to move pivotally relative to the shaft towards its first end and has a portion which is intended to be gripped by a user towards its second end. The lever can be connected to the rod to cause the rod to move relative to the shaft at a point between the first and second ends. For example, the lever can have an aperture, especially a slotted aperture, extending through it at which the lever is connected to the rod. The rod can extend through the aperture. The rod can be connected to the lever by means of a fastener which extends through the aperture.

The lever should preferably be pivoted at a point which is fixed relative to the shaft. The lever can be pivotally fastened at a point which is on the shaft. The lever can be pivotally fastened to an arm which extends outwardly from the shaft. The arm will normally be fastened rigidly to the shaft so that the lever does not move relative to the shaft at the point at which it is fastened to the arm.

Preferably, the lever has a knob which can be gripped by a user, to cause the shaft and the rod to be rotated about their common axis. The knob can be provided on the lever at or towards the second end of the lever. The knob is preferably mounted on the lever so that it can rotate relative to the lever.

Preferably, the instrument includes an incremental drive to cause the rod to translate along the shaft when the shaft and rod are rotated. The incremental drive can be provided by means of a threaded rod which is threadingly received in a bore in the knob on the lever. The knob can be advanced along the threaded rod when lever rotates.

In another aspect, the invention provides a tool for forming a cavity within a bone, which comprises:
a. a shaft,
b. a blade which is pivotally mounted on the shaft towards one end thereof,
c. a rod which is fastened to the blade, and which can slide within the shaft, to change the pivotal position of the blade relative to the shaft,
d. an incremental drive to cause the rod to translate along the shaft when the shaft and rod are rotated.

Preferably, the shaft has a slot formed in it into which the blade can be retracted. The blade can be fastened to the shaft by means of a pivot pin which extends across the slot.

Preferably, the distance from the pivot pin for the blade to at least one of the ends of the slot in the shaft, preferably each end of the slot in the shaft, is greater than the distance from the pivot pin to the end of the blade. This can facilitate retraction of the blade into the slot.

The blade can have two opposed cutting edges. This can enable the blade to be operated to cut the bone from either of two retracted positions.

Preferably, the tool has a handle having a bore in it for receiving the shaft so that the shaft can be rotated relative to the handle while the tool is gripped using the handle.

The tool can be used to form a cavity in a bone which is rotationally symmetrical about the axis of a tunnel through which the tool is inserted into the bone. The size of the cavity is dependent on the length of the blade in the tool. The shape of the cavity is dependent on the shape of the cutting edge of the blade, and on the movement of the blade relative to the shaft. It can be preferred to form a cavity which, when viewed from one side perpendicular to a plane which contains the axis of the access tunnel, is generally rounded. This can be facilitated by use of a blade which has a rounded cutting edge.

During the cutting operation, the tool is rotated about the axis which is defined by the shaft. During such rotation, the blade is gradually deployed from within the slot in the shaft. By pivoting the blade through an angle approaching 180°, while holding the shaft against movement relative to the bone, a cavity can be formed in the bone whose shape approaches that of a sphere. By pivoting the blade through an angle which is less than about 90°, a cavity can be formed in the bone whose shape approximately that of a segment of a circle when the cavity is viewed from one side perpendicular to a plane which contains the axis of the access tunnel. The shape of such a cavity is sometimes referred to as a segment of a sphere, being the portion of a sphere which is defined by a circular plane.

The blade should be shaped so that it does not protrude unacceptably from the slot in the shaft when it is retracted. This can effectively limit the width of the blade. The blade should be sufficiently wide that successive sweeps of the blade across the bone tissue when the blade is in use overlap. The end face of the blade can be slightly rounded when the blade is viewed from one side.

The tool of the invention can be made from materials which are commonly used in the manufacture of surgical instruments. Examples of such materials include metals such as certain stainless steels, and polymers such as polyolefins (especially polyethylenes and polypropylenes), polyamides, polyesters and polycarbonates. It will generally be preferred for the shaft and the rod and the blade, at least, to be formed from metallic materials.

In a further aspect, the invention provides a method of treating avascular necrosis in the head of a femur, which comprises:
a. locating necrotic bone tissue,
b. forming a bore in the bone extending from the lateral cortex through the femoral neck into the head of the femur,
c. inserting into the bore a tool which comprises a shaft, a blade which is pivotally mounted on the shaft towards one end thereof, and a rod which is fastened to the blade, and which can slide within the shaft, to change the pivotal position of the blade relative to the shaft, and
d. rotating the shaft, rod and blade about the axis of the bore, while progressively deploying the blade by moving it relative to the shaft about its pivot.

Embodiments of the invention will now be described by way of example with reference to the accompanying drawings, in which:

FIG. 1 is an isometric view, partially in section, through the tool of the invention, in place in a tunnel in the head of a femur.

Figure 2A:
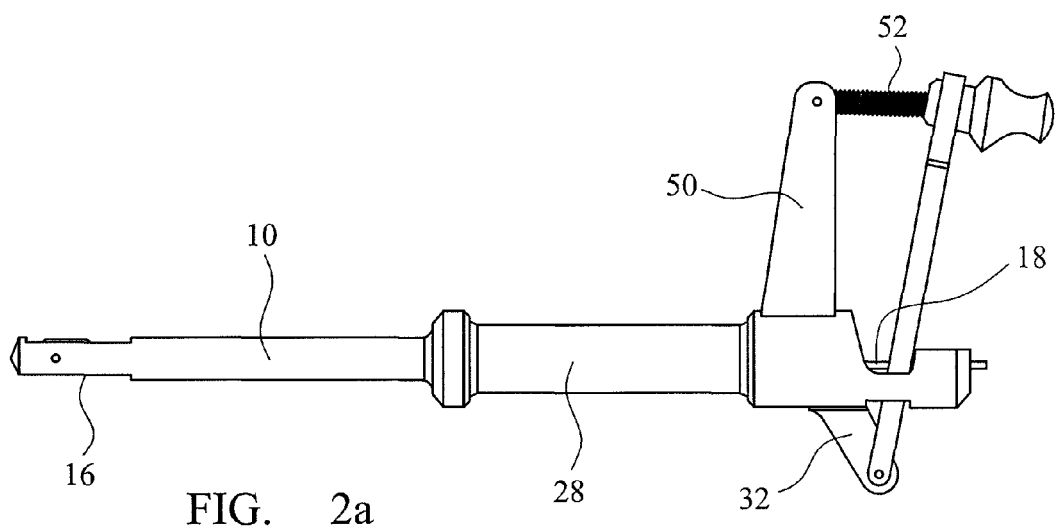
Figure 2B:
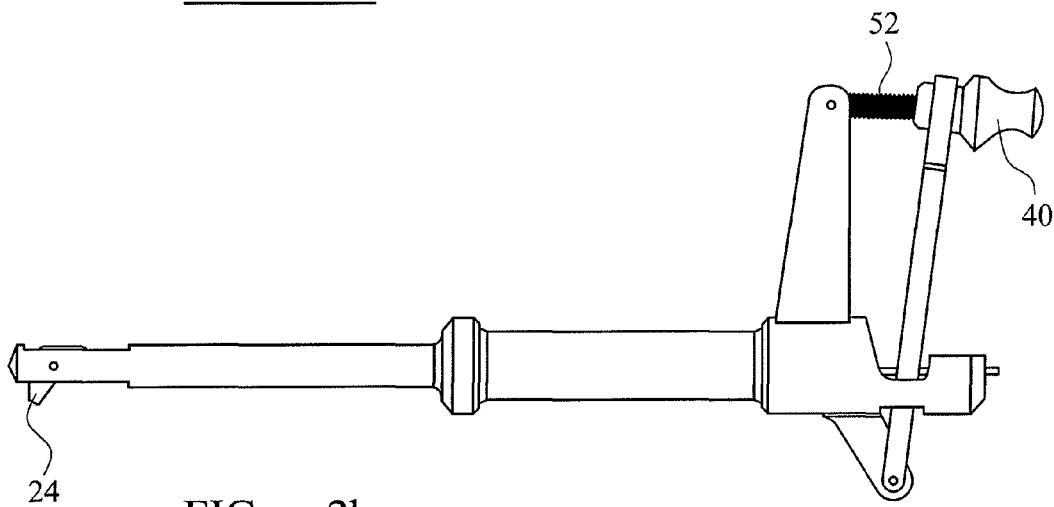
Figure 2C:
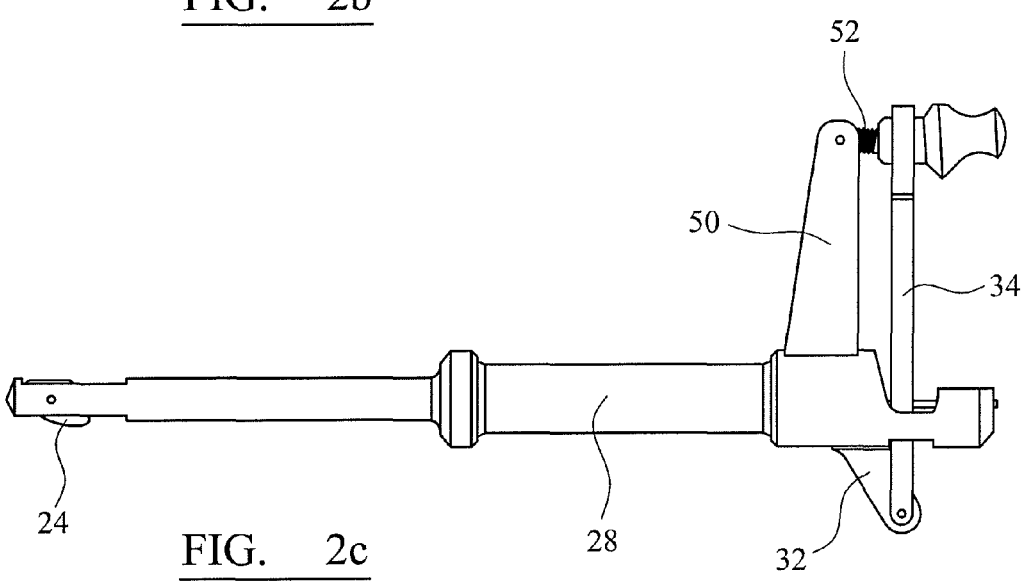

FIGS. 2*a* to 2*c* are side views of another embodiment of tool of the invention showing the blade in an initial retracted position, a deployed position, and a finished retracted position.

Referring to the drawings, FIG. 1 shows a cutting tool 2 inserted into a tunnel which extends medially through the neck 4 of a femur 6, from the lateral cortex into the head 8 of the femur. The tunnel is formed using a rotating cutting tool such as a drill or a reamer or using a combination of cutting tools. The tunnel extends into the head sufficiently so that the end of the tool is located in a region of the head in which the bone tissue is defective, for example as a result of loss of blood circulation to the bone tissue, such as when the patient is suffering from avascular necrosis.

The tool comprises a hollow shaft 10 having a blade end 12 and a handle end 14. The shaft has a blade slot 16 formed in its side wall at the blade end. A rod 18 extends through the shaft. A blade 20 is mounted to pivot within the blade slot on a pivot pin 22. The blade has a cutting portion 24 and a body portion 26. The pivot pin 22 passes through a hole in the body portion. The length of the blade slot 16 in the shaft 10 is slightly greater than twice the length of the blade measured from the pivot pin to the end of the blade, and the pin is located in the slot at a point which is approximately equidistant from the ends of the slot.

The rod 18 is connected at one end to the blade by means of a pin, at a point on the blade body portion 26 which is on the opposite side of the pivot pin from the cutting portion 24. The pin by which the rod is connected to the blade allows the blade to rotate within the blade slot relative to the rod. The blade can be made to pivot about the pivot pin 22 by moving the rod within the shaft.

The shaft has a handle 28 formed on it at the control end. The handle is wider than the shaft so that it can be gripped comfortably by a user. The rod 18 has an end portion 30 which extends beyond the end of the handle. The handle has a slot 31 formed in it, extending through its opposed side walls.

A lever support arm 32 extends from the handle 28. The lever support arm is formed integrally with the handle, for example in a manufacturing step which involves a moulding process such as injection moulding.

The tool includes a control arm 34. The control arm has an opening 36 extending through it in which the rod 18 is received, and held by means of a fastener 38 whose head is larger than the opening 36. Alternatively, the control arm might be fastened to the rod pivotally by means of a pin, as shown in FIGS. 2*a* to 2*c*. The control arm is pivotally connected at one end to the lever support arm, and extends through the slot 31 in the handle. Pivotal movement of the control arm 34 relative to the lever support arm 32 causes the rod 18 to move axially relative to the handle 28 and the shaft 10.

The control arm 34 has a knob 40 at its free end, which is free to rotate relative to the control arm. The knob is mounted on the control arm on a fastener which extends through an aperture in the control arm.

Use of the tool which is described above with reference to FIG. 1 is shown in FIGS. 2*a* to 2*c*. It will be understood that operation of the tool involves rotation of the tool about the axis of the shaft 10. This rotational movement is achieved by gripping the tool loosely using the handle 28 such that the handle can rotate within the user's hand. Rotational movement is then imparted using the knob 40 which is spaced from the axis of the shaft 10, by applying a torsional force to the knob 40 relative to the handle 28. When the blade 24 protrudes from the blade slot 16, the cutting edge on the blade causes bone tissue which is contacted by the blade to be shaved when the tool is rotated as described above.

The blade can be moved pivotally relative to the shaft between retracted and deployed positions by moving the rod within the shaft. This can be achieved by moving the control arm 34 about the pivot where it is connected to the lever support arm 32.

FIGS. 2*a* to 2*c* show another embodiment of the tool of the invention which includes an incremental drive to cause the rod to translate along the shaft when the shaft and rod are rotated. The incremental drive is provided by a drive support arm 50 which extends from is the shaft 10, in a direction which is opposite to the lever support arm 32. A drive rod 52 is pivotally connected to the drive support arm at its end. The drive rod has a left-handed thread formed on its outer surface.

The knob 40 has a threaded bore formed in it, so that it can threadingly receive the end of the threaded drive rod. Accordingly, as the knob is rotated relative to the drive rod and to the lever 34, the knob with the lever advances along the drive rod.

FIG. 2*a* shows a tool of the invention when the blade retracted within the blade slot such as it might be arranged before bone tissue has been cut. The knob 40 is located towards the free end of the drive rod 52.

FIG. 2*b* shows the tool of the invention when the blade when it has been deployed from within the blade slot. The knob 40 has been rotated so that it has advanced part way along the drive rod 52. Consequently, the rod 18 has advanced along the shaft 10, to cause the blade to be deployed.

FIG. 2c shows the tool of the invention when the blade when it has been retracted into the blade slot at the end of the cutting operation. The knob 40 has been rotated so that it has advanced fully along the drive rod 52. Consequently, the rod 18 has advanced along the shaft 10, to cause the blade to pivot beyond the deployed position to a position in which it is once again retracted into the blade slot.

The invention claimed is:

1. A tool for forming a cavity within a bone, comprising:
    a shaft having a distal end;
    a blade pivotally mounted on the shaft towards the distal end;
    a rod which is fastened to the blade, and which is slidable within the shaft to change the pivotal position of the blade relative to the shaft;
    a lever having an opening therein, the lever being connected to the rod, the rod extending through the opening; and
    an incremental drive configured to cause the rod to translate along the shaft when the shaft and rod are rotated, the incremental drive including a threaded rod having a distal rod end and a proximal rod end, the threaded rod being connected to the lever, and a knob having an internal thread, the internal thread of the knob being threaded with the threaded rod.

2. The tool of claim 1, wherein the knob can be gripped by a user such that the shaft and the rod can be rotated about the shaft axis.

3. The tool of claim 1, wherein the shaft has a slot formed therein into which the blade can be retracted.

4. The tool of claim 1, wherein the knob is movable relative to the shaft as a result of movement of the knob along the threaded rod.

5. The tool of claim 4, wherein the thread of the threaded rod is a left-handed thread, and the knob is configured such that when the knob is turned clockwise, the knob moves relative to the threaded rod from a first position to a second position, closer to the proximal rod end.

6. The tool of claim 1, wherein the rod is linked to the threaded rod so that the rod moves relative to the shaft when the knob moves relative to the threaded rod.

7. The tool of claim 1, wherein the threaded rod is approximately parallel to, and spaced apart from, the shaft.

8. A method of treating avascular necrosis in the head of a femur, comprising the steps of:
    forming a bore in the bone extending from the lateral cortex through the femoral neck into the head of the femur, the bore having a bore axis;
    inserting into the bore a tool comprising a shaft having a shaft axis and a distal end, a blade pivotally mounted on the shaft towards the distal end, a rod fastened to the blade at a pivot point and slidable within the shaft to change the pivotal position of the blade relative to the shaft, a lever having an opening therein, the lever being connected to the rod, the rod extending through the opening, a threaded rod, the threaded rod being connected to the lever, and a knob having an internal thread, the internal thread of the knob being threaded with the threaded rod; and
    rotating the knob relative to the threaded rod and rotating the shaft, rod and blade about the shaft axis so as to progressively deploy the blade by moving the blade relative to the shaft about the pivot point.

* * * * *